United States Patent [19]

Komatsu et al.

[11] Patent Number: 5,497,407
[45] Date of Patent: Mar. 5, 1996

[54] CONTAMINATING-ELEMENT ANALYZING METHOD

[75] Inventors: Fumio Komatsu, Fuchu; Kunihiro Miyazaki, Tokyo; Ayako Shimazaki, Yokohama, all of Japan

[73] Assignee: Kabushiki Kaisha Toshiba, Kawasaki, Japan

[21] Appl. No.: 158,272

[22] Filed: Nov. 29, 1993

[30] Foreign Application Priority Data

Dec. 1, 1992 [JP] Japan ................. 4-322033

[51] Int. Cl.$^6$ ................. G01N 23/223
[52] U.S. Cl. ................. 378/45; 378/49
[58] Field of Search ................. 378/45–49

[56] References Cited

U.S. PATENT DOCUMENTS 3,662,882  5/1972  Obermayer ................. 378/45

*Primary Examiner*—Craig E. Church
*Attorney, Agent, or Firm*—Oblon, Spivak, McClelland, Maier & Neustadt

[57] ABSTRACT

A contaminating-element analyzing method enables precise identification of contaminating elements and precise calculation of concentrations thereof by eliminating a broad peak waveform due to Rayleigh scattering and Compton scattering and a background waveform from a measured waveform of a contaminated sample. A blank sample or samples are irradiated by an X-ray beam under a constant condition to obtain a plurality of measured waveforms of fluorescent X-rays, and the plurality of measured waveforms are averaged to obtain a blank waveform. Then a contaminated sample is irradiated by the X-ray beam under the same condition as that for the blank sample to obtain a measured waveform of fluorescent X-rays. The blank waveform is subtracted from the measured waveform of contaminated sample, and then the contaminating elements are identified and the concentrations thereof are calculated on the basis of the waveform data after the subtraction process.

5 Claims, 5 Drawing Sheets

CONTAMINATING-ELEMENT ANALYZING METHOD

BACKGROUND OF THE INVENTION

1. Field of the Invention

The present invention relates to an element analyzing method using fluorescent X-rays, and more particularly to a contaminating-element analyzing method which make possible precise identification of contaminating elements and precise calculation of concentrations thereof.

2. Related Background Art

The X-ray fluorescence analysis has been used heretofore as a nondestructive element analysis for an object to be measured (sample). The total reflection X-ray fluorescence analysis was also developed to increase the sensitivity and is under study for applications to metal contamination control in semiconductor process (Ayako, SHIMAZAKI and Kuniharu, MIYAZAKI: NIKKEI MICRO DEVICE, p148 No. 86, August 1992). Among the total reflection X-ray fluorescence analyses, the energy dispersive X-ray fluorescence analysis is effective for measuring a spectrum in a wide energy range and therefore enables simultaneous analysis of multiple elements through a single solid-state detector (SSD) disposed immediately above the sample. Also, since the energy dispersive X-ray fluorescence analysis needs no analyzing crystal, the SSD can be set closer to the sample. For that reason, the energy dispersive method has a feature of higher sensitivity than that in the wave dispersive method in X-ray fluorescence analysis.

Further, the energy-dispersive total reflection X-ray fluorescence analysis is inferior in spectral resolution to the wavelength-dispersive analysis, providing a smaller total count number. Therefore, the total reflection method is likely to be affected by statistical error of counting.

In the total reflection X-ray fluorescence analysis there are various impeding peaks in addition to peaks from characteristic X-rays of elements in an initially measured waveform. That is, observed in the measured waveform are peaks specific to the SSD, for example sum peaks and escape peaks, or diffraction peaks if the Bragg condition is satisfied by angles among the primary X-ray, the sample and the SSD.

In addition to the peaks as described above, there appears a peak due to Rayleigh scattering, in which a characteristic X-ray of a material of rotating target as X-ray source is Rayleigh-scattered by the sample. For example, if the anticathode is made of a target material of W which has a high excitation efficiency for transition metals, a peak is detected at 9.671 keV of W-L$_{\beta 1}$. Additionally, when the characteristic X-ray of the anticathode material impinges on the sample, a part of the X-ray is subjected to Compton scattering, thereby to lose a part of energy when detected. As a result, the two types of scattering peaks (Rayleigh scattering peak and Compton scattering peak) are detected in the form of peak trailing on the low energy side (see FIGS. 2A and 2B).

Since the scattering peaks each have a broad spread on the low energy side, they are impeding peaks to the K$_\alpha$ peak (8.63 keV) of Zn, as shown in (a) in FIG. 3. The influence of such impeding peaks becomes outstanding in case of contamination in low concentration, which could be an error factor in identification of each analyzing element peak and in calculation of intensity thereof. In the case where the intensity of each contaminating element is calculated by the ROI (Region of Interest) method for example, it could become difficult to set a region for calculation. Also, if waveform separation is carried out based on the nonlinear optimization method, treatment of background could be difficult, which in turn results in making identification of peaks and calculation of intensities thereof difficult. This problem is caused by the waveform separation in which data of asymmetric waveform trailing on the low energy side due to the Compton scattering is replaced by a symmetric Gaussian function.

SUMMARY OF THE INVENTION

The present invention has been accomplished by taking the points as described into consideration. It is an object of the present invention to provide a contaminating-element analyzing method which enables precise identification of analytical elements and precise calculation of concentrations thereof while keeping minimum the influence of Rayleigh scattering and Compton scattering of the characteristic X-ray of anticathode material.

A contaminating-element analyzing method according to the present invention comprises a step of irradiating a blank sample or blank samples with an X-ray under a constant condition to obtain a plurality of measured waveforms of fluorescent X-rays and averaging the plurality of measured waveforms of fluorescent X-rays to obtain a blank waveform, a step of irradiating a contaminated sample with the X-ray under the same condition as that for the blank sample to obtain a measured waveform of fluorescent X-rays, a step of subtracting the blank waveform from the measured waveform of the contaminated sample, and a step of identifying contaminating elements and obtaining concentrations thereof, based on the waveform data obtained by the subtraction.

The method of the invention permits only a waveform of objective contaminating elements to be extracted, because the subtraction of the blank waveform, which is obtained by averaging the plurality of measured waveforms of blank sample(s), from the measured waveform of contaminated sample eliminates the broad scattering peaks caused by the Rayleigh scattering and the Compton scattering and the background waveform.

DESCRIPTION OF THE PREFERRED EMBODIMENT

An embodiment of the present invention will now be described in detail with reference to the accompanying drawings. FIG. 1 to FIG. 5 illustrate an embodiment of contaminating-element analyzing method according to the present invention.

Figure 5:
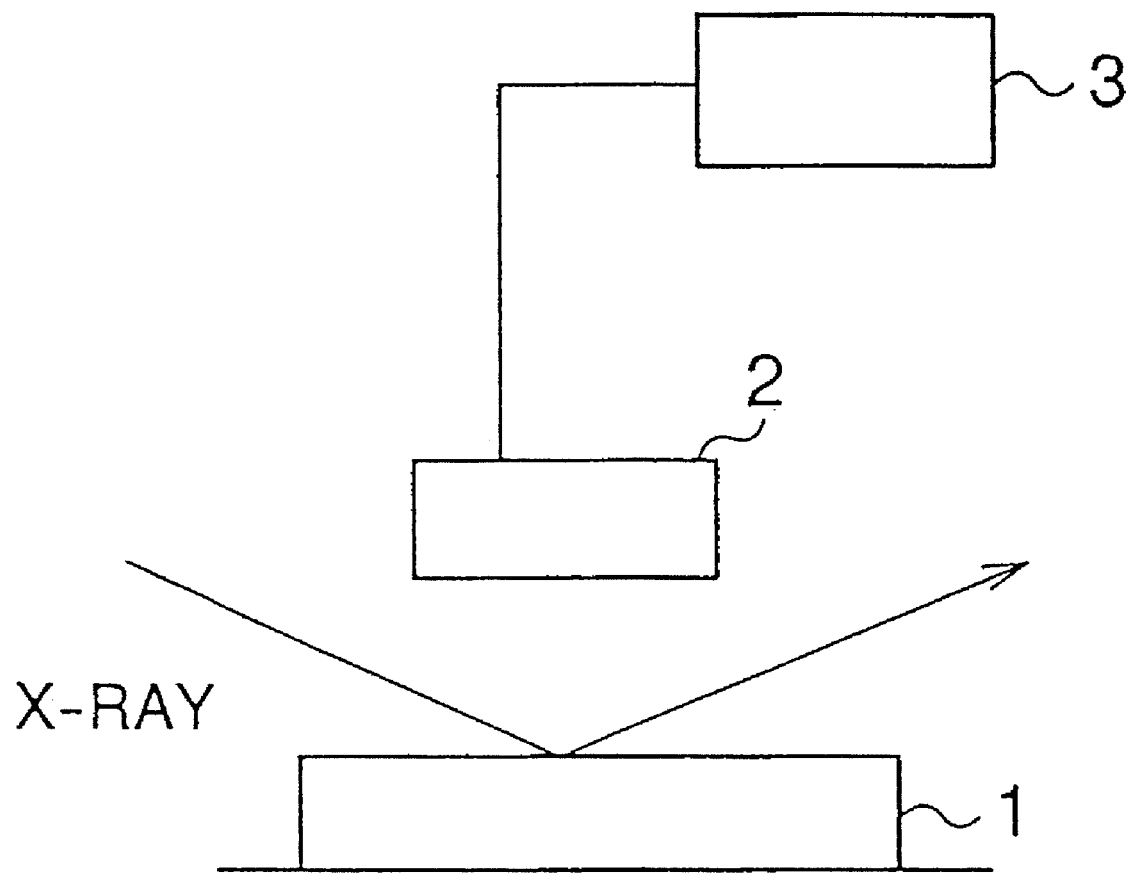
FIG. 5 is a schematic view showing an energy dispersive X-ray fluorescence analyzing apparatus.

The energy dispersive X-ray fluorescence analyzing apparatus will be first schematically described referring to FIG. 5. In FIG. 5, an X-ray is radiated to impinge on a sample 1 (an object to be measured) such as a semiconductor wafer made of Si, and fluorescent X-rays generated from the sample 1 are detected by a solid-state detector 2 (SSD). Connected to the solid-state detector 2 is a signal processing unit 3, which processes electric signals output from the solid-state detector 2.

Next, with reference to FIG. 1 to FIG. 5, a contaminating-element analyzing method using the energy dispersive X-ray fluorescence analyzing apparatus will be described.

Figure 1:
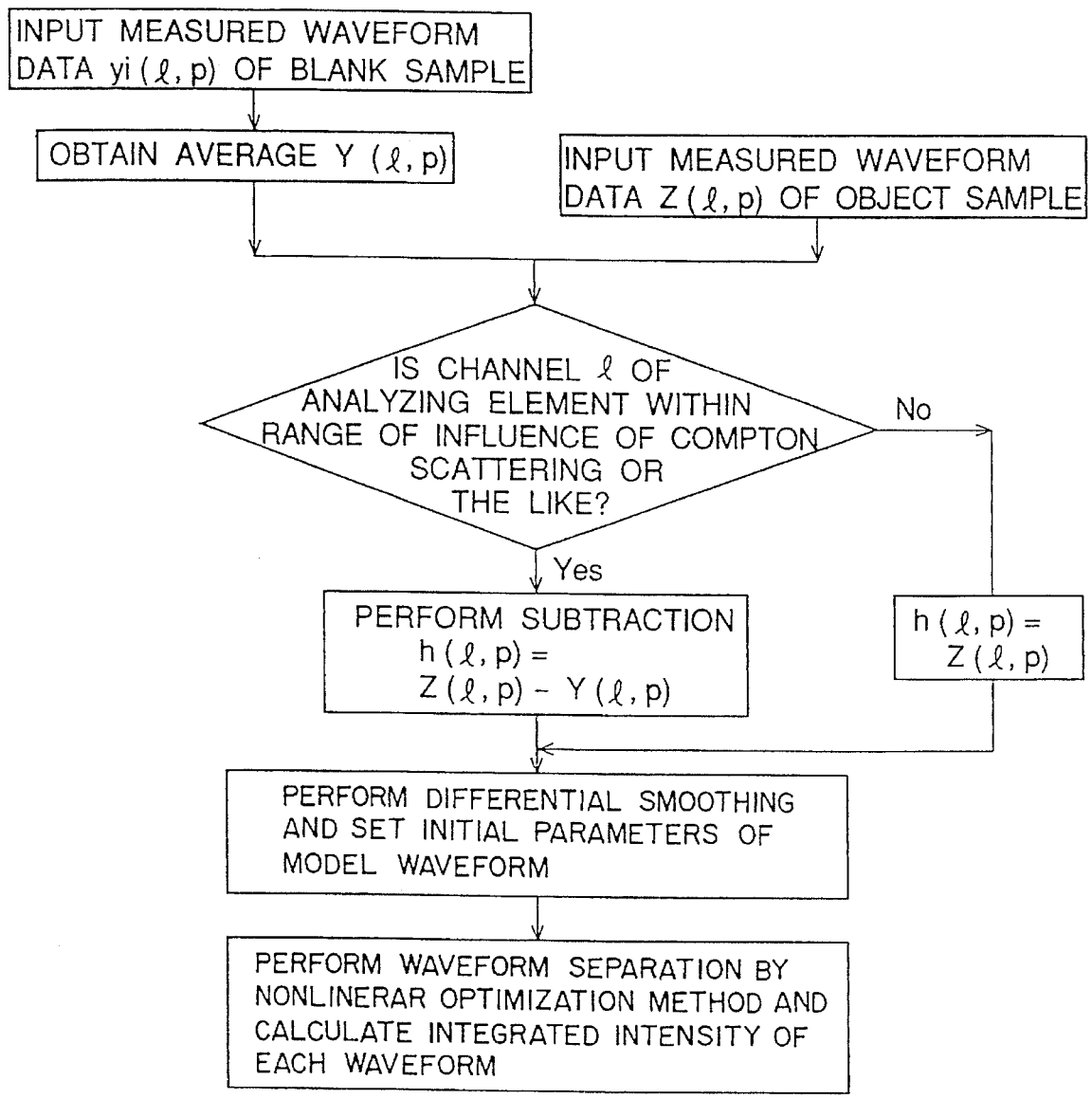
FIG. 1 is a flowchart to illustrate an embodiment of contaminating-element analyzing method according to the present invention.
Figure 2A:
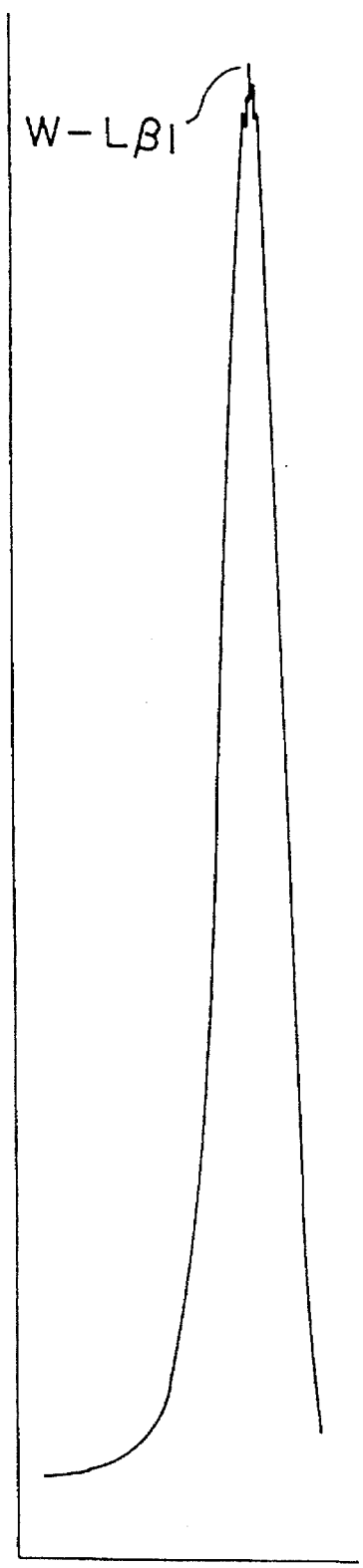
FIG. 2A is a graph showing data of a measured waveform of a blank sample in a specific example of contaminating-element analyzing method according to the present invention.
Figure 2B:
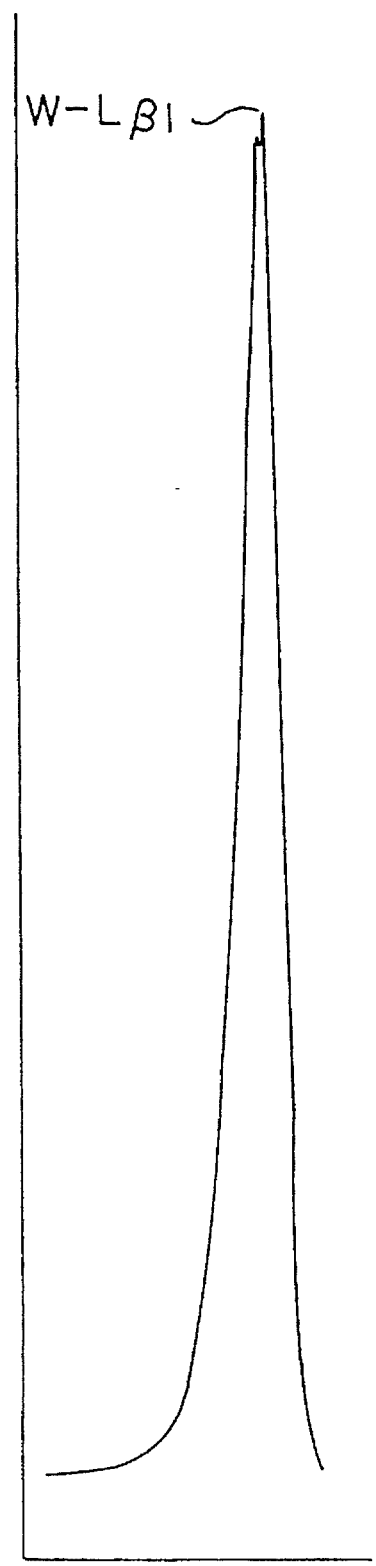
FIG. 2B is a graph showing data of a blank waveform obtained by averaging data of measured waveforms.

The X-ray is guided to irradiate a blank sample 1 containing no contaminating element, as shown in FIG. 1, and fluorescent X-rays thus generated by the sample 1 are detected by the solid-state detector 2. A measured waveform of fluorescent X-rays of the blank sample is then input into the signal processing unit 3.

A plurality (N) of measured waveform data $Y_i$ (1, p) of a blank sample or blank samples are input into the unit. In the data $Y_i$ (1, p), 1 represents a channel and p measurement parameters as will be described hereinafter. The plurality of measured waveform data may be obtained at plural points on a single blank sample or on different blank samples under the constant conditions of voltage on the anticathode, current, irradiation conditions such as X-ray incident angle and measurement time (measurement parameters (p)). An arithmetic mean is obtained from the measured waveform data of blank sample(s) (as will be referred to as an averaging process) to as obtain blank waveform data Y (1, p) as a reference. That is, the data of blank waveform is calculated as follows.

$$Y(1,p) = \left( \sum_{i=1}^{N} y_i(1,p) \right) / N \qquad (1)$$

In the equation, 1 represents each channel (corresponding to an energy value) which was processed by a pulse processor. If $W\text{-}L_{\beta1}$ is used as incident X-ray source for example, the range of 1 should be considered in the energy range affected by the Rayleigh scattering and the Compton scattering, which is approximately 8.3 keV<1<10.0 keV. In Equation (1) p represents the measurement parameters.

The thus obtained blank waveform data Y (1, p) should be waveform data which is a combination of (i), a signal waveform of $W\text{-}L_{\beta1}$ trailing on the low energy side due to the Rayleigh scattering and the Compton scattering of incident X-ray, with (ii) the background waveform.

Such an averaging process can improve the statistical error of counting of data in each channel. Specifically, a sufficient number of data of blank sample is in the range of from 4 to 16 (which improves the SN ratio (Signal to Noise ratio) 2 to 4 times). In more detail, with the number N of data, the signal amount is kept unchanged in averaging. In other words, the signal amount increases N times in addition, but the increased signal amount is averaged (as 1/N times), resulting in making the signal amount constant. In contrast, a noise amount decreases $1/\sqrt{N}$ times. Accordingly, the SN ratio increases $\sqrt{N}$ times. Then, if the number of data is 4 to 16, the SN ratio can be improved $\sqrt{4}$ to $\sqrt{16}$ times (i.e., 2 to 4 times).

Then a sample to be measured (contaminated sample) including contaminating elements is irradiated by the X-ray under the same irradiation conditions (with the same measurement parameters) as those for the blank sample to obtain a measured waveform of fluorescent X-rays, and the obtained measured waveform data Z (1, p) is input into the signal processing unit 3.

If a channel 1 of an analyzing element is within the energy range (8.3<1<10.0) which is under influence of the Rayleigh scattering and the Compton scattering, the blank waveform data is subtracted from the measured waveform data of the contaminated sample, as follows.

$$h(1, p) = Z(1, p) - Y(1, p) \qquad (2)$$

If even one of the measurement parameters p upon X-ray irradiation on the contaminated sample is different from that for the blank sample, another blank waveform data is selected from data base as to coincide all the measurement parameters with each other.

The waveform data h (1, p) after the subtraction is waveform data including only a $K_\alpha$ spectrum waveform of objective contaminating elements extracted from the measured waveform data Z (1, p) of the contaminated sample including the $K_\alpha$ spectrum waveform of all existing elements, the broad peak of $W\text{-}L_{\beta1}$ due to the Rayleigh scattering and the Compton scattering of incident X-ray, and the background waveform. The subtraction process is not carried out if a channel 1 of an analyzing element is out of the energy range affected by the Rayleigh scattering and the Compton scattering.

The contaminating elements are next discriminated from each other and concentrations thereof are obtained on the basis of the waveform data h (1, p) obtained by the subtraction process. A differential smoothing process is first carried out for the waveform data. The smoothing is done with five points, taking an energy band width and an energy resolution of each channel (each point on the horizontal axis in waveform data). Then zero points are detected in the differential waveform as candidates for peaks in the waveform data.

A model function, for example a Gaussian function, is prepared for each peak in the waveform data. Then a model waveform is constituted by a linear sum of Gaussian functions thus prepared. In this case, each Gaussian function has initial parameters of energy position u, peak height $h_0$ and half width of half maximum w, which are variables for each Gaussian function.

The model waveform can be expressed as follows:

$$z(1, p) = \Sigma_j h_0 \exp\{-\ln 2(1-u)^2/w^2\}.$$

(where j corresponds to each peak detected).

The energy position u of each Gaussian function can be approximately determined by a channel number i corresponding to each peak in the waveform data. The peak height $h_0$ can be approximately determined from each peak in the waveform data. Further, each half width at half maximum can be approximately determined on the basis of a point where a third differential of each function takes 0.

A nonlinear optimization process is next carried out to determine the aforementioned initial parameters so that the residual sum of squares is minimized between the waveform data and the model waveform constituted by the linear sum of Gaussian functions prepared for all peaks in the waveform data. Thus this process provides separate waveforms of Gaussian functions. In more detail, an objective function e (1) is defined as follows by the residual sum of squares between the model waveform z (1, p) and the measured waveform data h (1, p):

$$e(1)=\Sigma\{z(1, p)\text{-}31\ h(1, p)\}^2$$

where $$z(1, p)=\Sigma_j h_0.exp\{-ln2(1-u)^2/w^2\}$$

(where j corresponds to each peak detected).

Vector variables ($h_0$, u, w) to minimize the objective function e (1) are obtained by using the nonlinear optimization method based on the simplex method. It should be noted that another technique may be employed in place of the simplex method.

The energy positions of separated waveforms are then compared one by one with $K_\alpha$ radiation peak positions of elements, based on the separated waveforms of Gaussian functions obtained by the nonlinear optimization process. The comparison is performed with a certain margin taking a chemical shift into consideration. If a Gaussian function is found at a $K_\alpha$ radiation peak position of an element within the margin, the Gaussian function is identified as the element (contaminating element). If a peak has no corresponding element, it is identified as one of escape peaks, sum peaks and background noises. Next obtained is an integrated intensity (area) of each Gaussian function for corresponding element. In this case, each Gaussian function is integrated in the range of ±4w, where w is the half width at half maximum of Gaussian function.

In the present embodiment the subtraction process of blank waveform from the measured waveform of a contaminated sample can eliminate the broad peak of $W-L_{\beta 1}$ due to the Rayleigh scattering and the Compton scattering and the background waveform so as to extract only a waveform of $K_\alpha$ spectra of contaminating elements to be detected. For that purpose, the model waveform is constituted by the differential smoothing process, and the waveform separation process is performed by the nonlinear optimization method, whereby the identification of contaminating elements and the calculation of concentrations thereof can be conducted with precision.

The identification of contaminating elements and the calculation of concentrations thereof can be performed by applying the ROI method to the waveform data obtained by subtracting the blank waveform from the measured waveform of contaminated sample. In this case, the subtraction process can correct the broad asymmetric peak shape caused by the Rayleigh scattering and the Compton scattering, so that the identification of contaminating elements and the calculation of concentrations thereof can be done with precision by the ROI method.

The ROI (Region of Interest) method is carried out as follows. An integral interval is manually set for a peak to be calculated in the measured spectra, and a total integral intensity is calculated in that interval. Then an intensity of background is calculated in the same integral interval. The obtained background intensity is subtracted from the total integral intensity to obtain the integrated intensity of object peak.

It is sometimes difficult to manually set an integral interval for an asymmetric peak in the ROI method. The correction of shape can facilitate the setting of integral interval, which enables precise calculation of integrated intensity.

SPECIFIC EXAMPLE

A specific example of the present invention is next described with FIG. 2A to FIG. 4. FIG. 2B shows a blank waveform obtained by the averaging process with data of measured waveforms of the blank sample. This blank waveform was obtained under the condition that the energy range was from 8.33 keV to 10.0 keV and the number of waveform data was four. The blank waveform shown in FIG. 2B is greatly improved in fluctuation caused by the statistical error of counting as compared with the measured waveform data of blank sample without the averaging process (shown in FIG. 2A).

Figure 3:
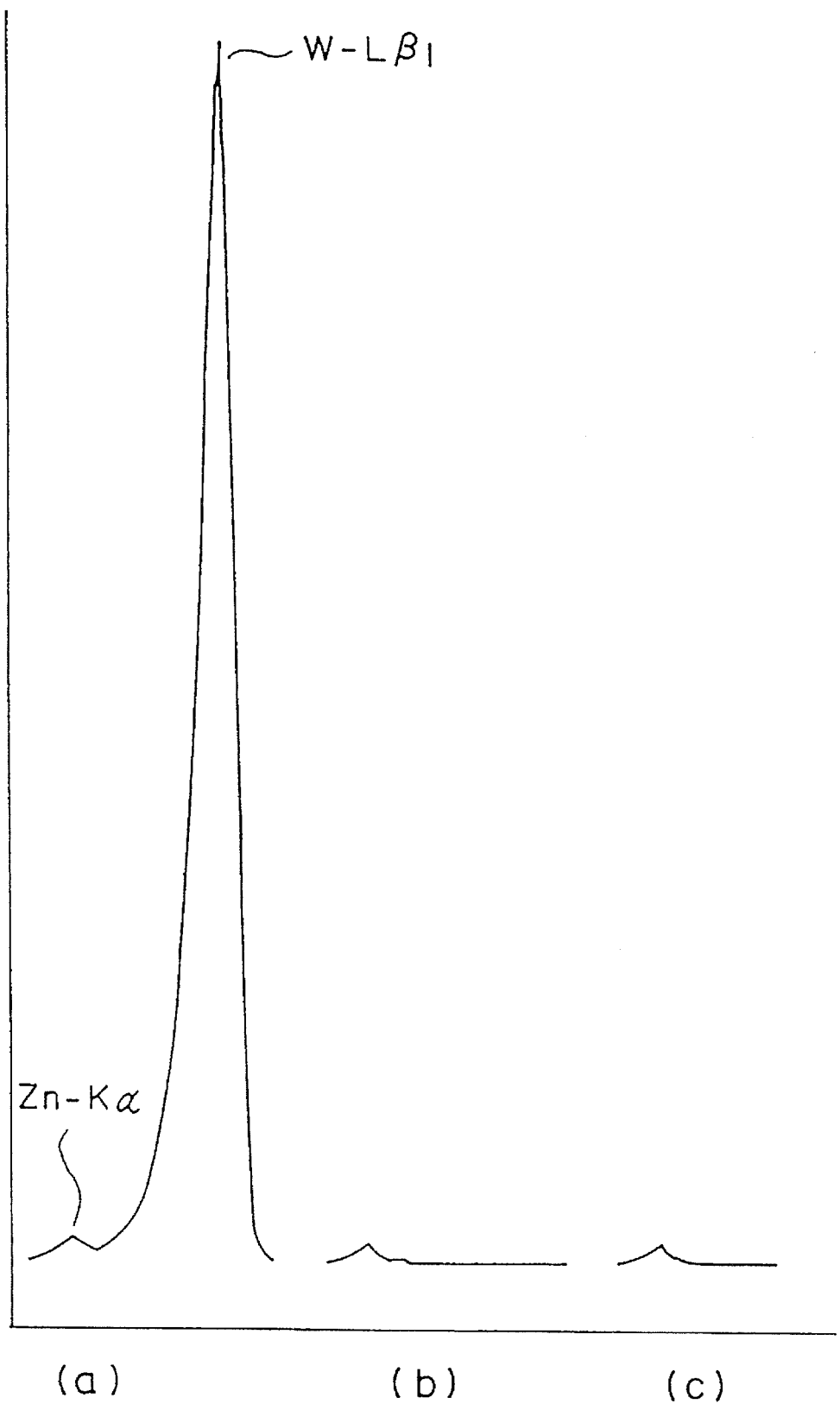
FIG. 3 is a graph showing data of a measured waveform of a contaminated sample in a specific example of contaminating-element analyzing method according to the present invention, waveform data after a subtraction process, and waveform data after a smoothing process.

In FIG. 3 (a) is shown a measured waveform in the same energy range for a contaminated sample containing a contaminating element (Zn). It is seen in (a) in FIG. 3 that a $Zn-K_\alpha$ spectrum is superimposed on a broad tail of incident X-ray caused by the Compton scattering. FIG. 3 shows in (b) a waveform obtained by subtracting the averaged blank waveform from the measured waveform of the contaminated sample. FIG. 3 also shows in (c) a waveform obtained by further processing the subtracted waveform data by a 5-point-weighted smoothing process. As shown in (c) in FIG. 3, only the $Zn-K_\alpha$ peak is extracted while canceling the broad peak of $W-L_{\beta 1}$ due to the Rayleigh scattering and the Compton scattering of incident X-ray and the background waveform. Therefore, in assigning an integral region by the conventional ROI method, the interval can be readily set for the object contaminating element, which reduces errors.

Figure 4:
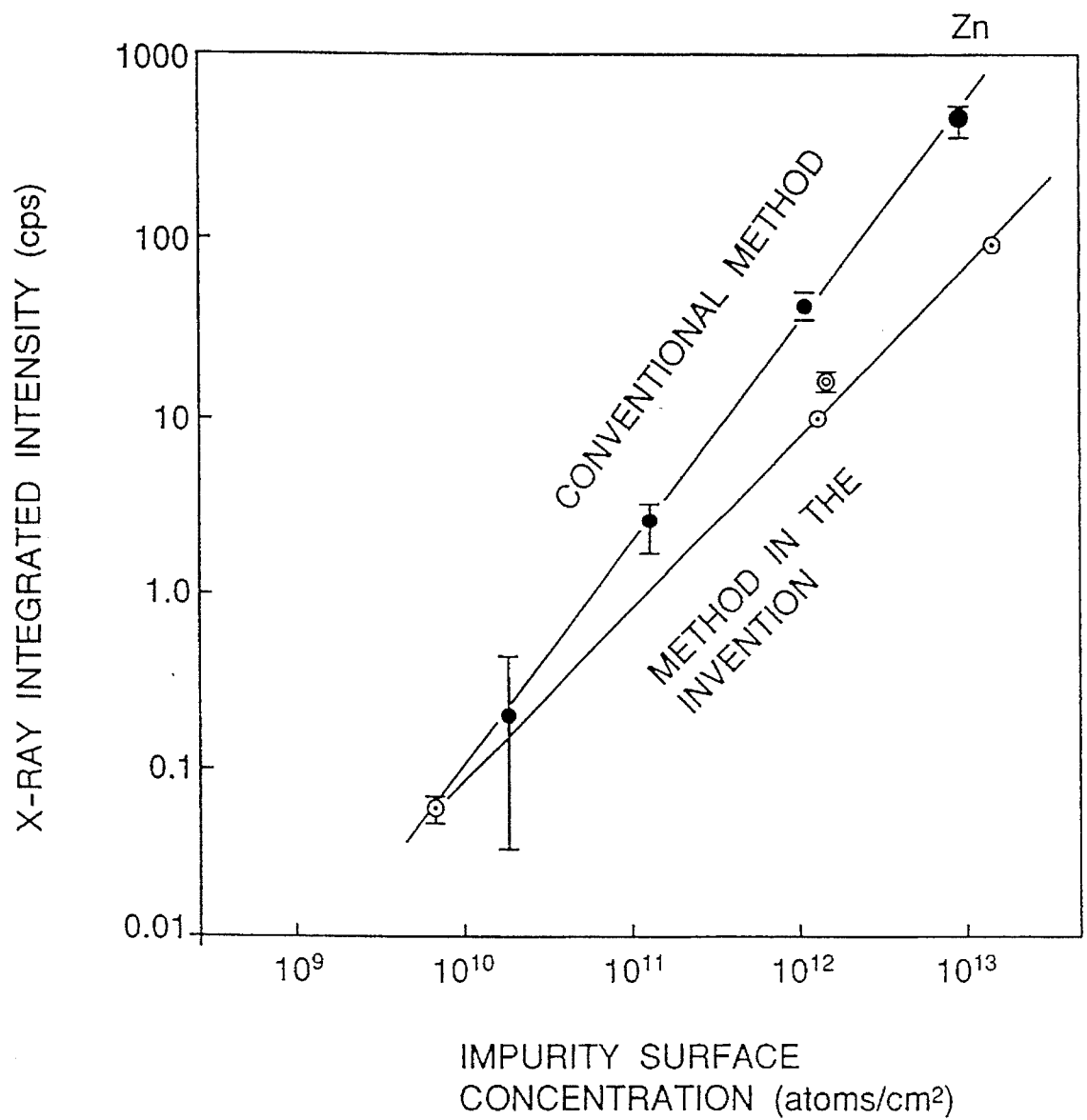
FIG. 4 is a graph showing a calibration curve representing the relation between surface impurity concentration and X-ray integrated intensity in the present invention together with that in a conventional method.

FIG. 4 shows integrated intensities of Zn, which were calculated for the waveform data including only the $Zn-K_\alpha$ peak extracted by the subtraction process after the waveform separation process based on the nonlinear optimization method. A detection limit is $1\times10^{10}$ atoms/cm$^2$ in the conventional method in which the subtraction process of blank waveform is not carried out. The conventional method increases the measurement dispersion in concentration of the order of $10^{10}$. In contrast, it is seen that the method according to the present invention can permit the measurement of a sample containing $7\times10^9$ atoms/cm$^2$ of contaminating element with less dispersion. As shown in FIG. 4, the method according to the present invention makes possible precise measurement even if there are mixed impeding spectra and background greater in intensity than the $K_\alpha$ spectrum. This is also verified in FIG. 4 in that the calibration curve is close to an inclination of 45° in the method according to the present invention.

As described above, the present invention is effective for extracting only the waveform of object contaminating elements by eliminating the broad peak waveform due to the Rayleigh scattering and the Compton scattering and the background waveform from the measured waveform of the contaminated sample. Therefore, the identification of contaminating elements and the calculation of concentrations thereof can be carried out with precision.

What is claimed is:

1. A contaminating-element analyzing method, comprising the steps of:

irradiating a blank sample plural times with an X-ray beam under a constant condition;

detecting, after each irradiation of the blank sample has terminated, a measured spectrum of fluorescent X-rays having broad scattering peaks caused by Rayleigh scattering and Compton scattering;

averaging plural measured spectra of fluorescent X-rays to obtain a blank spectrum;

irradiating a contaminated sample with the X-ray beam under the same condition as that for the blank sample;

detecting, after irradiation of the contaminated sample has terminated, a measured spectrum of fluorescent X-rays having broad scattering peaks caused by Rayleigh scattering and Compton scattering;

subtracting said blank spectrum from said measured spectrum of the contaminated sample so as to eliminate the broad scattering peaks; and identifying a contaminating element and obtaining the concentration thereof, on the basis of the spectrum data obtained at said subtracting step.

2. A contaminating-element analyzing method according to claim 1, wherein, at the step of obtaining a blank spectrum, the total number of the plurality of measured spectrum of fluorescent X-rays to be averaged is in the range of from 4 to 16.

3. A contaminating-element analyzing method according to claim 1, wherein, at the step of obtaining a blank spectrum, the X-ray beam is radiated onto the blank sample with a voltage on the anticathode, a current, an X-ray incident angle and an X-ray irradiation time which are kept constant.

4. A contaminating-element analyzing method according to claim 1, wherein said step of identifying a contaminating element and obtaining a concentration thereof comprises steps of:

performing differential smoothing for a measured spectrum to detect peaks in the measured spectrum;

preparing a model function for each peak in the measured spectrum with variables of initial parameters and constituting a model spectrum by obtaining a linear sum of the model functions;

performing a nonlinear optimization process to minimize the residual sum of squares between the model spectrum and the measured spectrum, thereby determining the initial parameters of each model function so as to obtain separated spectra; and identifying the contaminating element, on the basis of the separated spectra, and obtaining an integrated intensity of a separate spectrum for the identified contaminating element.

5. A contaminating-element analyzing method according to claim 1, wherein said step of identifying a contaminating element and obtaining the concentration thereof is carried out on the basis of the region of interest method.

* * * * *